United States Patent
Garritano et al.

(10) Patent No.: US 6,931,915 B2
(45) Date of Patent: Aug. 23, 2005

(54) WIDE RANGE DYNAMIC RHEOMETER

(75) Inventors: Ronald F. Garritano, Monroe Township, NJ (US); John P. Berting, Wilmington, DE (US); Paul G. Mode, Cranford, NJ (US)

(73) Assignee: TA Instruments, Newcastle, DE (US)

( * ) Notice: Subject to any disclaimer, the term of this patent is extended or adjusted under 35 U.S.C. 154(b) by 0 days.

(21) Appl. No.: 10/459,056

(22) Filed: Jun. 10, 2003

(65) Prior Publication Data

US 2004/0250605 A1 Dec. 16, 2004

(51) Int. Cl.[7] .......................... G01N 11/00; G01N 11/14
(52) U.S. Cl. ..................... 73/54.42; 73/54.02; 73/54.33
(58) Field of Search .............................. 73/54.02, 54.33, 73/54.34, 54.37, 54.39, 843, 54.42

(56) References Cited

U.S. PATENT DOCUMENTS

| | | | | |
|---|---|---|---|---|
| 4,501,155 A | * | 2/1985 | Garritano ..................... | 73/847 |
| 4,601,195 A | * | 7/1986 | Garritano ..................... | 73/54.34 |
| 5,520,042 A | * | 5/1996 | Garritano et al. ........... | 73/54.02 |

* cited by examiner

Primary Examiner—Daniel S. Larkin
(74) Attorney, Agent, or Firm—Aslan Baghdadi; Pillsbury Winthrop Shaw Pittman LLP (57) ABSTRACT

A rheometer includes a holder assembly for coupling a test specimen to a motor assembly to effect rotational strain in the test specimen while enabling the determination of axial displacement effected by the test specimen normal to the direction of the rotational strain, the holder assembly having a first member coupled to the test specimen, a second member coupled to the motor assembly, and a suspension arrangement coupling the first member with the second member for simultaneous maximum resistance to relative rotational displacement between the first and second members and minimum resistance to relative axial displacement between the first and second members. Information pertaining to the axial displacement, and to the temperature of the test specimen, is obtained through measuring circuits which include sensors placed in moving component parts of the rheometer and is delivered to an external processor through information transmission systems which include an induction arrangement for transmitting the information while maintaining the desired minimum resistance to the relative axial displacement. Power is delivered to the measuring circuits through a power transfer system which includes a similar induction arrangement.

14 Claims, 6 Drawing Sheets

WIDE RANGE DYNAMIC RHEOMETER

The present invention relates generally to the measurement of physical properties of materials and pertains, more specifically, to improvements in rheometers for performing a complete range of steady, dynamic and transient rheological analyses in sample materials ranging from lower viscosity fluids, dispersions and gels to higher viscosity polymer melts.

The testing of materials for rheological characteristics has assumed a greater role as the development of more specialized materials continues to grow. An increased reliance upon quick and accurate testing protocols has led to a demand for simplified and versatile rheological instruments which can yield accurate results throughout a wide diversity of testing environments, with greater ease of operation.

As set further in U.S. Pat. No. 4,501,155, it has been found advantageous, from the standpoint of shortening the time required for performing particular rheological tests, to apply a precise stress to a test specimen and then measure the resulting strain. It has been demonstrated that under these circumstances, the various forces in the test specimen will come to equilibrium more quickly, providing accurate test results in a more expeditious manner. Further, as discussed in U.S. Pat. No. 4,601,195, where the test specimen is in the form of a disk-like configuration and is coupled between axially spaced apart, radially-extending surfaces for the application of stress to test the specimen, it has been observed that the test specimen has a tendency to expand axially, in a direction normal to the radially-extending surfaces, requiring that the measuring devices provide some degree of compliance in order to accommodate and measure this axial, or normal, displacement.

From the standpoint of accuracy, as well as quick response, it would be advantageous to be able to measure more directly these axial displacements experienced during dynamic testing of the test specimen through the placement of measurement sensors directly in the moving component parts of a dynamic rheometer and the extraction of measurement information from these sensors without introducing any significant effect on the movements of the moving component parts. In addition, the measurement of other test parameters, such as temperature, as well as displacements, could be attained with increased accuracy and quicker response by placing appropriate measurement sensors directly in the moving component parts so as to enable the extraction of measurement information from locations more proximate to the site where the information pertaining to these test parameters is generated. Moreover, the ability to power an electronic measurement system which includes measurement sensors placed in these moving component parts without compromising the ability of the component parts to move independent of external influences would enable a greater degree of accuracy than heretofore available in dynamic rheometers. By obtaining such direct readings of the test parameters being measured, measurements can be obtained more quickly and with greater accuracy, and without the necessity for extrapolations or computations in order to determine the true magnitude of the parameters indicative of the rheological characteristics being measured.

The present invention enables measurements to be obtained directly at the moving components of a dynamic rheometer for quicker response and greater accuracy in the measurement of test parameters indicative of the rheological characteristics of a test specimen. As such, the present invention attains several objects and advantages, some of which are summarized as follows: Provides an improvement in an advanced rheometer capable of performing a complete range of steady, dynamic and transient rheological analyses on sample materials ranging from low viscosity fluids, dispersions and gels to high viscosity polymer melts; enables the accomplishment of rheological testing in less time, with increased accuracy and across a wider range of performance specifications than heretofore available; raises the overall quality of measurements attained with a rheometer; accomplishes normal displacement measurements and temperature measurements in rheological test specimens with increased ease and greater accuracy; assures increased control over measurements in rheological test specimens for greater accuracy; enables simultaneous testing for a wide range of simultaneous analyses; accommodates a wide range of environmental conditions with minimal requirements at testing sites; enables direct readings of test parameters being measured, through powered electronic systems having sensors placed in moving component parts of a rheometer, in close proximity to sites where the desired test information is generated; provides increased reliability for exemplary performance over an extended service life.

The above objects and advantages, as well as further objects and advantages, are attained by the present invention which may be described briefly as an improvement in a rheometer in which a test specimen is subjected to a torque about a given axis in the rheometer to effect strain in the test specimen about the given axis, the improvement comprising: a first member; a first coupler for coupling the first member to the test specimen while the test specimen is subjected to an applied torque; a second member; a second coupler for coupling the second member to a motor assembly for transmitting torque from the motor assembly to the second member; a coupling arrangement coupling the first member with the second member for movement of the second member in circumferential directions about the given axis, corresponding to the strain effected in the test specimen about the given axis, and for relative axial displacement between the first member and the second member along the given axis; an axial position information sensor for providing information pertaining to axial position of the first member relative to the second member; an axial position information transmitter circuit for receiving axial position information from the axial position information sensor, the axial position information transmitter circuit being movable through movements corresponding to movement of the second member in the circumferential directions about the given axis; an axial position information receptor circuit juxtaposed with the axial position information transmitter circuit and placed in a stationary location relative to the axial position information transmitter circuit; an isolator arrangement isolating the stationary axial position information receptor circuit mechanically and electrically from the movable axial position information transmitter circuit; and an axial position information transfer system for passing axial position information from the movable axial position information transmitter circuit across the isolator arrangement to the stationary axial position information receptor circuit without a direct mechanical or electrical connection between the movable axial position information transmitter circuit and the stationary axial position information receptor circuit.

In addition, the present invention includes an improvement in a rheometer in which strain is effected in a test specimen while temperature is measured in the test specimen, the improvement comprising: a test specimen temperature information sensor for juxtaposition in close proximity with the test specimen to provide information pertaining to the temperature of the test specimen; a test specimen temperature information transmitter circuit for receiving test specimen temperature information from the test specimen temperature information sensor; the test specimen temperature information sensor and the test specimen temperature information transmitter circuit being movable through movements corresponding to the strain effected in the test specimen; a test specimen temperature information receptor circuit juxtaposed with the test specimen temperature information transmitter circuit and being placed at a stationary location relative to the test specimen temperature information transmitter circuit; an isolator arrangement isolating the stationary test specimen temperature information receptor circuit mechanically and electrically from the movable test specimen temperature information transmitter circuit; and a temperature information transfer system for passing test specimen temperature information from the movable test specimen temperature information transmitter circuit across the isolator arrangement to the stationary test specimen temperature information receptor circuit without a direct mechanical or electrical connection between the movable test specimen temperature information transmitter circuit and the stationary test specimen temperature information receptor circuit.

Further, the present invention includes an improvement in a rheometer in which strain is effected in a test specimen in order to measure a test parameter in the test specimen, the improvement comprising: a test parameter information sensor for juxtaposition in close proximity with the test specimen to provide information pertaining to the test parameter of the test specimen; a test parameter information transmitter circuit for receiving test parameter information from the test parameter information sensor; the test parameter information sensor and the test parameter information transmitter circuit being movable through movements corresponding to the strain effected in the test specimen; a test parameter information receptor circuit juxtaposed with the test parameter information transmitter circuit and being placed at a stationary location relative to the test parameter information transmitter circuit; an isolator arrangement isolating the stationary test parameter information receptor circuit mechanically and electrically from the movable test parameter information transmitter circuit; and a test parameter information transfer system for passing test parameter information from the movable test parameter information transmitter circuit across the isolator arrangement to the stationary test parameter information receptor circuit without a direct mechanical or electrical connection between the movable test parameter information transmitter circuit and the stationary test parameter information receptor circuit.

Still further, the present invention includes an improvement in a rheometer having a holder assembly for holding a test specimen subjected to a torque about a given axis in the rheometer to effect strain in the test specimen about the given axis and simultaneous highly compliant relative displacement between the test specimen and the holder assembly in directions along the given axis, within a prescribed range of axial displacement, as the test specimen is subjected to the measured torque, the holder assembly comprising: a first member; a first coupler for coupling the first member to the test specimen while the test specimen is subjected to an applied torque; a second member; a second coupler for coupling the second member to a motor assembly for transmitting torque from the motor assembly to the second member; a coupling arrangement coupling the first member with the second member for movement of the second member in circumferential directions about the given axis, corresponding to the strain effected in the test specimen about the given axis, the coupling arrangement including a plurality of suspension elements essentially rigid in the circumferential directions about the given axis and highly compliant in axial directions along the given axis, the suspension elements being oriented for transmitting torque from the second member to the first member with maximum resistance to relative rotational displacement between the first member and the second member about the given axis, and with minimum resistance to relative axial displacement between the first member and the second member along the given axis, within the prescribed range of axial displacement.

The invention will be understood more fully, while still further objects and advantages will become apparent, in the following detailed description of a preferred embodiment of the invention illustrated in the accompanying drawing, in which.

Figure 1:
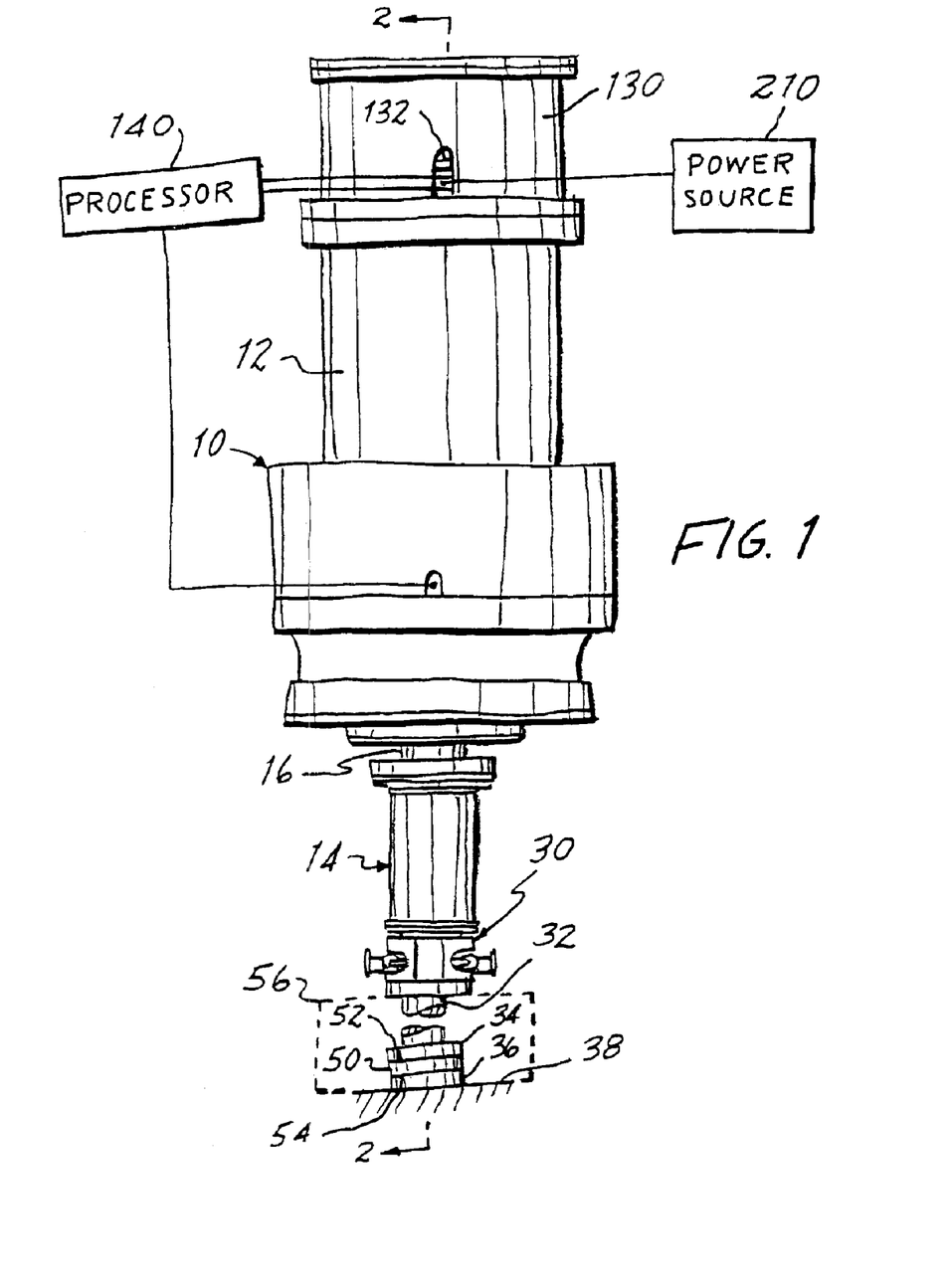
FIG. 1 is a pictorial, partially diagrammatic elevational view of a rheometer utilizing improvements of the present invention.
Figure 2:
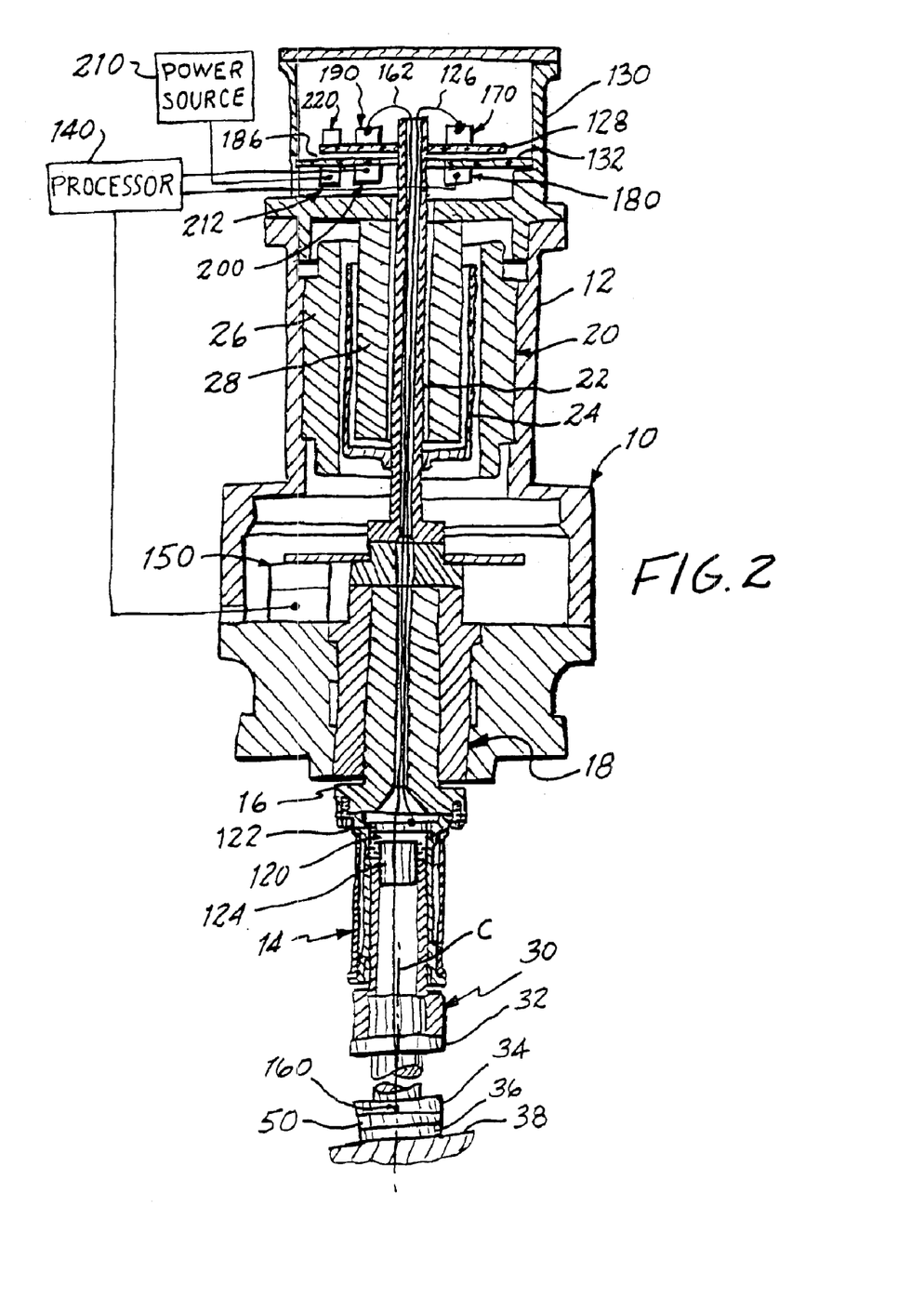
FIG. 2 is an enlarged, longitudinal cross-sectional view taken along line 2—2 of FIG. 1.

Referring now to the drawing, and especially to FIGS. 1 and 2 thereof, a rheometer is shown at 10 and is seen to include a housing 12 and a holder assembly in the form of a depending quill 14 coupled at the upper end of the quill 14 to an upper shaft 16 extending axially upwardly through an air bearing 18 to a motor assembly 20 having a central shaft 22 coupled to a drag cup 24 placed between the stator 26 and the corepiece 28 of motor assembly 20, in an arrangement similar to that described in detail in the aforesaid U.S. Pat. No. 4,501,155, the disclosure of which patent is incorporated herein by reference thereto. A clamp assembly 30 at the lower end of the quill 14 selectively clamps a fixture 32 to the quill 14, and the fixture 32 includes a platen 34 which is juxtaposed with a table 36 supported on and affixed to stationary base 38 of the rheometer 10.

As an example of an operation to be performed utilizing rheometer 10, a test specimen is shown as specimen 50 is placed between the platen 34 and the table 36. Specimen 50 is in the form of a disk of a polymer to be subjected to a predetermined measured torque for the purpose of determining rheological characteristics of the polymer. To that end, specimen 50 is affixed to the platen 34 along an upper surface 52 of the specimen and is affixed to the table 36 along a lower surface 54 of the specimen 50, as described in the aforesaid U.S. Pat. No. 4,501,155. Viscoelastic properties of specimen 50 are to be measured under an elevated temperature, and an oven 56 is provided for maintaining the specimen 50 at a desired elevated temperature. A precise torque applied to central shaft 22 is transmitted through upper shaft 16 to quill 14 and specimen 50, thereby applying a predetermined stress to specimen 50 and producing a rotational displacement of platen 34, about an axis C, corresponding to strain in specimen 50. At the same time, specimen 50 will exert an axially upward force upon platen 34, as described in the aforesaid U.S. Pat. No. 4,601,195, the disclosure of which patent is incorporated herein by reference thereto, tending to displace the platen 34 upwardly along axis C.

Figure 3:
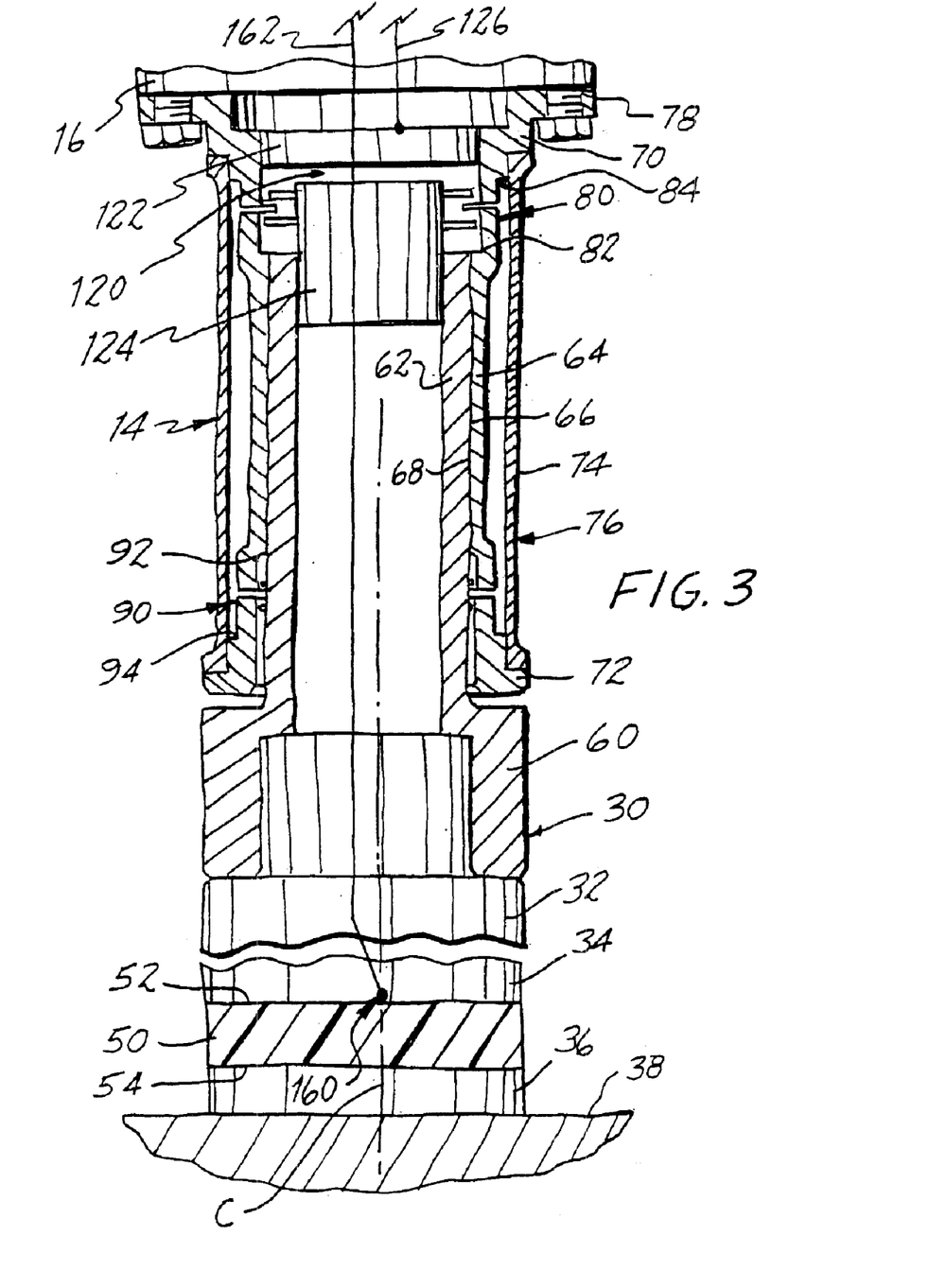
FIG. 3 is a further enlarged, longitudinal cross-sectional view of a fragment of FIG. 2.

In order to attain a high degree of accuracy in the measurement of this particular test parameter, while enabling the simultaneous rotational displacement and axial displacement of the platen 34 over a wider range of measurements, quill 14 is provided with a construction which resists relative rotational movement between the platen 34 and the quill 14, in response to torque transmitted to quill 14 and specimen 50, while simultaneously permitting highly compliant axial movement of the platen 34 relative to quill 14, in response to axial forces exerted upon the platen 34 by the specimen 50. Turning now to FIG. 3, clamp assembly 30 includes a clamp 60 carried by a tubular post 62 which extends upwardly into a first member in the form of a tubular cylindrical section 64, the relative dimensions of outer surface 66 of post 62 and inner surface 68 of cylindrical section 64 being such that the post 62 is secured within the cylindrical section 64 by an interference fit, so that any relative movement between the post 62 and the cylindrical section 64 is precluded. Thus, clamp assembly 30 serves as a coupler for coupling the specimen 50, through fixture 32, to cylindrical section 64. Cylindrical section 64 extends along the axis C and is coaxial with a second member shown in the form of an upper tubular cylindrical section 70 and a lower tubular cylindrical section 72 joined together by an outer sleeve 74 made integral with the sections 70 and 72 such that the sections 70 and 72 and the sleeve 74 comprise a single rigid structure 76. A flange 78 at the upper end of cylindrical section 70 serves as a coupler for coupling the rigid structure 76 of quill 14 to the motor assembly 20, through upper shaft 16 and air bearing 18.

A coupling arrangement couples the cylindrical section 64 with the upper and lower cylindrical sections 70 and 72 such that there is provided a maximum resistance to relative rotational movement between the cylindrical section 64 and the upper and lower cylindrical sections 70 and 72, while providing minimal resistance to relative axial movement between the cylindrical section 64 and the upper and lower cylindrical sections 70 and 72. To this end, an upper suspension system 80 couples the upper end 82 of section 64 with the confronting lower end 84 of the upper section 70, and a lower suspension system 90 couples the lower end 92 of section 64 with the confronting upper end 94 of the lower section 72. Thus, section 64 is suspended within the rigid structure 76, coaxial with the cylindrical sections 70 and 72.

Figures 4, 5:
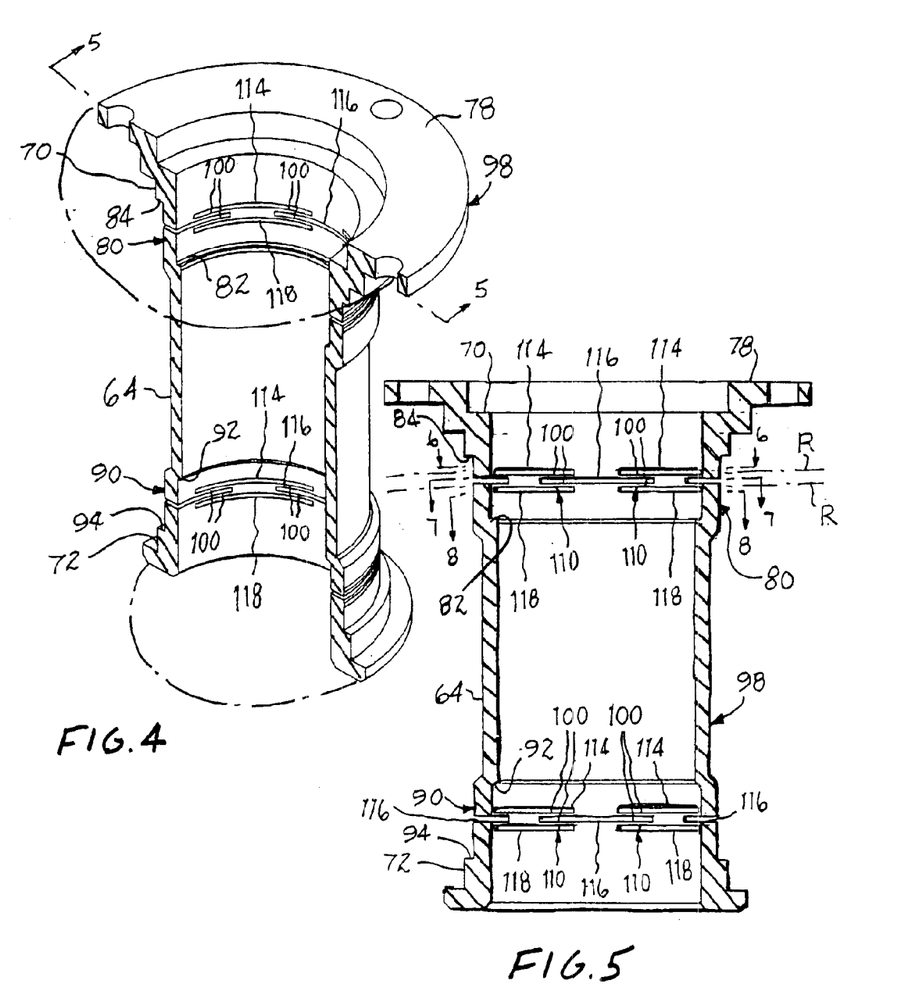
FIG. 4 is a pictorial view of a component part of the fragment shown in FIG. 3, cut away to show internal structure.
FIG. 5 is a longitudinal cross-sectional view of the component part of FIG. 4, taken along line 5—5 of FIG. 4.

In the preferred construction, cylindrical sections 64, 70 and 72 are parts of a one-piece, unitary tubular member shown at 98 in FIGS. 4 and 5. Each suspension system 80 and 90 includes a plurality of suspension elements shown in the form of leaf springs 100 oriented for transmitting torque from the upper and lower cylindrical sections 70 and 72, respectively, to the cylindrical section 64 with maximum resistance to relative rotational displacement between the cylindrical section 64 and the upper and lower cylindrical sections 70 and 72 about axis C, and with minimum resistance to relative axial displacement between the cylindrical section 64 and the upper and lower cylindrical sections 70 and 72 along axis C, at least within a prescribed range of relative axial displacement. In the preferred construction, leaf springs 100 lie in radial planes R normal to axis C and are spaced circumferentially from one another around the axis C. Placement of the essentially flat leaf springs 100 in radial planes R provides rigidity in circumferential directions for resisting relative displacement between section 64 and sections 70 and 72 in circumferential directions, while permitting highly compliant relative axial displacements, in directions normal to radial planes R.

Figure 6:
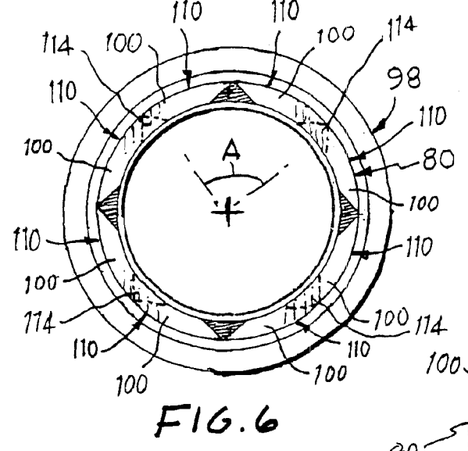
FIGS. 6 through 8 are lateral cross-sectional views taken along lines 6—6, 7—7 and 8—8, respectively, of FIG. 5.
Figure 7:
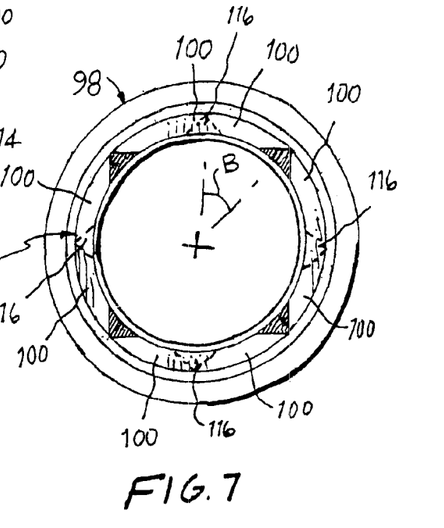
Figure 8:
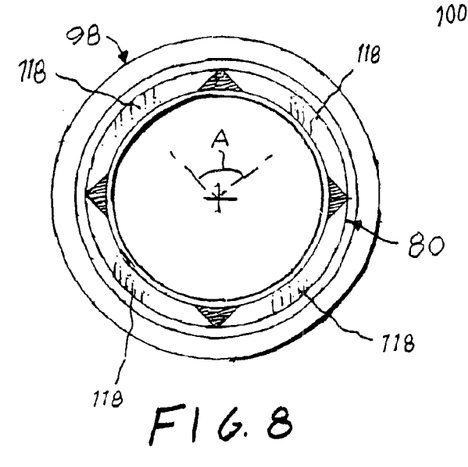

As best seen in FIGS. 6 through 8, as well as in FIGS. 4 and 5, leaf springs 100 are arranged in stacks 110 of juxtaposed leaf springs 100, the stacks 110 being spaced circumferentially from one another in a symmetrical pattern around the axis C to establish a balanced array of leaf springs 100 around axis C. In the construction illustrated in connection with the preferred embodiment, the single tubular member 98 is constructed of relatively rigid material, such as steel or titanium, with suspension systems 80 and 90 formed unitary with sections 64, 70 and 72 by cutting sets of slots 114, 116 and 118 between the confronting ends 82, 84 and 92, 94 to establish at least two circumferentially overlapping leaf springs 100 in each stack 110. The sets of slots 114, 116 and 118 are spaced apart axially, and the slots 114, 116 and 118 of each set are spaced apart circumferentially by angles A of 90°. The set of slots 116 is rotated at an angle B of 45° relative to the sets of slots 114 and 118 to establish the circumferentially overlapping arrangement of leaf springs 100 in each stack 110. The leaf springs 100 are thick enough in axial directions to act as rigid columns in circumferential directions for resisting relative displacement between section 64 and sections 70 and 72 in circumferential directions. However, the leaf springs 100 are thin enough in axial directions to be quite flexible and highly compliant in axial directions, enabling relative axial displacement with minimal resistance. The combination of maximum resistance to relative circumferential movement and minimal resistance to relative axial movement provides rheometer 10 with the ability to accomplish accurate measurements over wider ranges of movements, thereby accommodating test specimens of materials ranging from lower viscosity fluids, dispersions and gels to higher viscosity polymer melts, all with simplified testing protocols.

Returning now to FIGS. 2 and 3, an axial position sensor in the form of a proximity transducer 120 provides information pertaining to the axial displacement of section 64 relative to sections 70 and 72. Transducer 120 includes a first transducer element 122 fixed within upper section 70 and a second transducer element 124 affixed within section 64, through post 62, proximate first transducer element 122. Information pertaining to relative axial displacement between section 64 and section 70 is conducted, in the form of axial position information, via a conductor 126, from the first transducer element 124 to a transmitter circuit board in the form of a disk 128 placed within an upper portion 130 of housing 12 and secured to the central shaft 22 for rotation with the central shaft 22. A receptor circuit board 132 is fixed within the upper portion 130 of housing 12, is stationary, and is juxtaposed with and in close proximity to the disk 128 and receives the axial position information for delivery to an external processor 140, in a manner set forth in detail below. The construction of quill 14, as described above, enables an accurate determination of axial displacements and, consequently, axial position over a wider range for the ready accommodation of an extended variety of materials to be tested.

A rotational position sensor in the form of a transducer 150 provides information pertaining to the rotational displacement of the platen 34 relative to the table 36 and provides a measurement of the strain in specimen 50, as set forth in detain in the aforesaid U.S. Pat. No. 4,501,155, which information is delivered to processor 140.

A temperature sensor in the form of a thermistor 160 is placed in platen 34 in juxtaposition with and in close proximity to specimen 50 and provides information pertaining to the temperature of the specimen 50 itself during measurement of the axial and rotational displacements set forth above. The specimen temperature information is conducted, via a conductor 162, from the thermistor 160 to the transmitter circuit board provided in the form of disk 128. The receptor circuit board 132 receives the temperature information for delivery to the processor 140, all as discussed in greater detail below.

Figure 9:
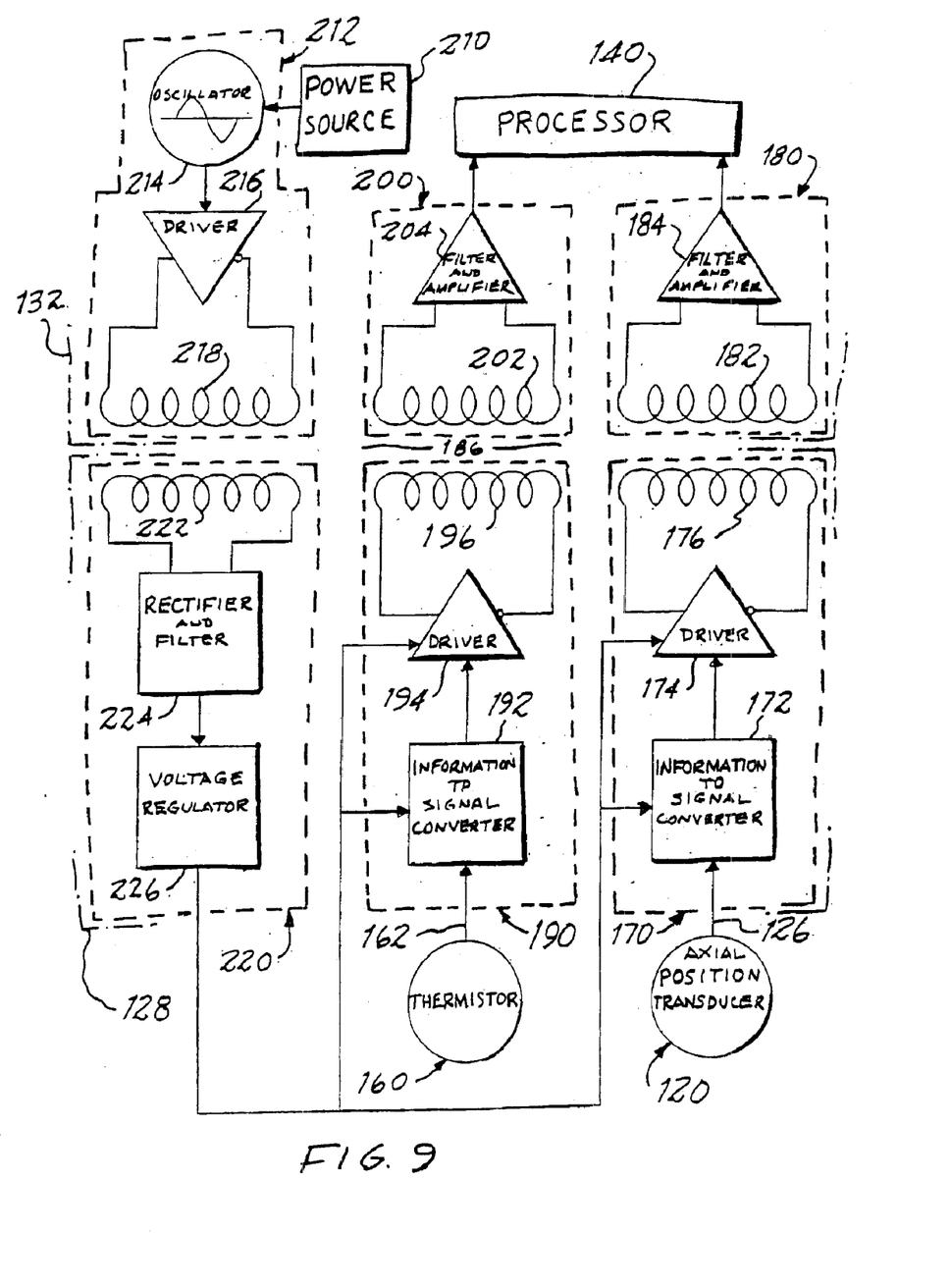
FIG. 9 is a diagrammatic illustration of a system for delivering information obtained from a test specimen in the rheometer to an external processor.

Turning now to FIG. 9, as well as to FIG. 2, delivery of the axial position information and the specimen temperature information to external processor 140 is accomplished without disturbing or otherwise affecting any rotational displacement and, consequently, any axial displacement of the platen 34 so that a very high degree of accuracy is maintained. To this end, axial position information from transducer 120 is conducted, via conductor 126, to an axial position information signal transmitter circuit 170 carried by movable disk 128. An axial position information signal receptor circuit 180 is carried by stationary receptor circuit board 132. An isolator arrangement includes a gap 186 between the disk 128 and the receptor circuit board 132 for providing both mechanical and electrical isolation between the disk 128 and the receptor circuit board 132. The axial position information signal is transferred from the axial position information signal transmitter circuit 170 to the axial position information signal receptor circuit 180 by an information transfer system which maintains mechanical and electrical isolation and assures the desired accuracy in the measurement of axial displacement. In the illustrated embodiment, the information transfer system accomplishes the transfer of the axial position information by an induction arrangement. Thus, axial position information signal transmitter circuit 170 includes an information-to-signal converter 172 for converting the information received from transducer 120 into a corresponding axial position information signal, a signal driver 174 and an axial position information signal primary coil 176, all carried by the disk 128. Axial position information signal receptor circuit 180 includes a secondary coil 182 and a high pass filter and amplifier 184. The gap 186 establishes a transformer air gap between the primary coil 176 and the secondary coil 182. The axial position information signal is passed by induction from the primary coil 176 to the secondary coil 182 so as to maintain mechanical and electrical isolation and assure the desired accuracy. The high pass filter and amplifier 184 then derives the axial position information from the axial position information signal and delivers the axial position information to external processor 140.

In a like manner, specimen temperature information is transferred by an information transfer system which maintains mechanical and electrical isolation and assures the desired accuracy in the measurement of temperature of the specimen 50. Thus, in the illustrated embodiment, specimen temperature information from thermistor 160 is conducted, via conductor 162, to a specimen temperature information signal transmitter circuit 190 carried by movable disk 128. Specimen temperature information signal transmitter circuit 190 includes a signal converter 192 for converting the specimen temperature information received from thermistor 160 into a specimen temperature information signal, a signal driver 194 and a specimen temperature signal primary coil 196, all carried by the disk 128. A specimen temperature information signal receptor circuit 200 is carried by receptor circuit board 132 and includes a secondary coil 202 and a high pass filter and amplifier 204. As before, gap 186 provides both mechanical and electrical isolation between the disk 128 and the receptor circuit board 132, and a transformer air gap between the primary coil 196 and the secondary coil 202. The specimen temperature information signal is passed by induction from the primary coil 196 to the secondary coil 202 so as to maintain mechanical and electrical isolation and assure the desired accuracy. The high pass filter and amplifier 204 then derives the specimen temperature information from the specimen temperature information signal and delivers the specimen temperature information to external processor 140.

Power is provided by a power transfer system to the axial position information signal transmitter circuit 170 and to the specimen temperature information signal transmitter circuit 190 without disturbing the mechanical and electrical isolation established by gap 186 between the disk 128 and the receptor circuit board 132. Thus, a DC power source 210 supplies power to a power source circuit 212 carried by the receptor circuit board 132. The power source circuit 212 includes an oscillator 214, a power driver 216, and a power source primary coil 218. A power supply circuit 220 is carried by the disk 128 and includes a power supply secondary coil 222 juxtaposed with the power source secondary coil 216 in an induction arrangement for receiving power from the power source primary coil 216 by induction. Power supply secondary coil 222 is coupled to a rectifier and filter 224 for delivering DC power through a voltage regulator 226 to the axial position information signal transmitter circuit 170 and to the specimen temperature signal transmitter circuit 190.

The arrangement provided by the signal transmitter circuits 170 and 190, and the signal receptor circuits 180 and 200, together with the gap 186, enables information pertaining to the measurement of test parameters which determine rheological characteristics of the specimen 50 to be obtained in close proximity to the site where the information is generated and to be delivered to processor 140 without any mechanical or electrical connection which otherwise could interfere with unfettered circumferential displacement or axial displacement corresponding to the strain induced in the specimen 50 during the testing procedure. Placement of thermistor 160 within the moving platen 34 allows temperature measurement to be accomplished proximate the site where temperature information is generated, enabling a direct reading of temperature for enhanced accuracy, without the need for extrapolation or computations to derive an actual temperature, as well as quicker response. Likewise, the arrangement provided by the power source circuit 212 and the juxtaposed power supply circuit 220, together with the gap 186, enables powering of the information signal transmitter circuits 170 and 190 without having a measurable effect on the relative circumferential and axial displacements.

It is noted that the delivery of information and power through the above-described transfer systems requires electrical isolation of each signal from the others in order to avoid corruption of the individual signals. The required isolation can be accomplished by transmitting each signal by means of a given frequency range, assigning a different range of frequencies to each signal and employing filters to isolate the signals. For example, the power circuits 212 and 220 could operate at 50 KHz, while the temperature signal circuits 190 and 200 would operate at 500 KHz and the axial position information signal circuits 170 and 180 would operate at 5 MHz. In this manner, isolation is accomplished readily with simple filters placed in the receptor circuits, as illustrated at 184 and 204 in FIG. 9. Other arrangements utilizing time division multiplexing of binary information, alternating frequencies, or the widths of alternating pulses are feasible.

While in the illustrated embodiment each transfer system comprises an induction arrangement, it will be apparent that alternate arrangements are available for accomplishing the transfer of position and temperature information, as well as power. Such arrangements include optical systems in which LEDs are modulated to transmit information signals, and capacitance systems in which information signals are transmitted by capacitance coupling. Each of these systems enables the direct measurement of displacements and temperatures utilizing powered measuring sensors placed in moving components of a rheometer for enhanced accuracy and quick response through the ability to read directly the test parameters being measured in close proximity to the site where the desired information is being generated.

It will be seen that the present invention attains all of the objects and advantages summarized above, namely: Provides an improvement in an advanced rheometer capable of performing a complete range of steady, dynamic and transient rheological analyses on sample materials ranging from low viscosity fluids, dispersions and gels to high viscosity polymer melts; enables the accomplishment of rheological testing in less time, with increased accuracy and across a wider range of performance specifications than heretofore available; raises the overall quality of measurements attained with a rheometer; accomplishes normal displacement measurements and temperature measurements in rheological test specimens with increased ease and greater accuracy; assures increased control over measurements in rheological test specimens for greater accuracy; enables simultaneous testing for a wide range of simultaneous analyses; accommodates a wide range of environmental conditions with minimal requirements at testing sites; enables direct readings of test parameters being measured, through powered electronic systems having sensors placed in moving component parts of a rheometer, in close proximity to sites where the desired test information is generated; provides increased reliability for exemplary performance over an extended service life.

It is to be understood that the above detailed description of a preferred embodiment of the invention is provided by way of example only. Various details of design and construction may be modified without departing from the true spirit and scope of the invention, as set forth in the appended claims.

The embodiments of the invention in which an exclusive property or privilege is claimed are defined as follows:

1. An improvement in a rheometer in which strain is effected in a test specimen while temperature is measured in the test specimen, the improvement comprising:
   a test specimen temperature information sensor for juxtaposition in close proximity with the test specimen to provide information pertaining to the temperature of the test specimen;
   a test specimen temperature information transmitter circuit for receiving test specimen temperature information from the test specimen temperature information sensor;
   the test specimen temperature information sensor and the test specimen temperature information transmitter circuit being movable through movements corresponding to the strain effected in the test specimen;
   a test specimen temperature information receptor circuit juxtaposed with the test specimen temperature information transmitter circuit and being placed at a stationary location relative to the test specimen temperature information transmitter circuit;
   an isolator arrangement isolating the stationary test specimen temperature information receptor circuit mechanically and electrically from the movable test specimen temperature information transmitter circuit; and
   a temperature information transfer system for passing test specimen temperature information from the movable test specimen temperature information transmitter circuit across the isolator arrangement to the stationary test specimen temperature information receptor circuit without a direct mechanical or electrical connection between the movable test specimen temperature information transmitter circuit and the stationary test specimen temperature information receptor circuit.

2. The improvement of claim 1 wherein the temperature information transfer system comprises an induction arrangement including a primary induction coil in the test specimen temperature information transmitter circuit, and a secondary induction coil in the test specimen temperature information receptor circuit and juxtaposed with the primary induction coil for receiving, by induction, test specimen temperature information from the primary induction coil.

3. The improvement of claim 2 wherein the isolator arrangement includes an air gap between the primary induction coil and the secondary induction coil.

4. The improvement of claim 1, including:
   a source of power;
   a power transmitter circuit placed in a stationary location relative to the test specimen temperature information transmitter circuit and being connected to the source of power;
   a power receptor circuit juxtaposed with the power transmitter circuit for receiving power from the power transmitter circuit, the power receptor circuit being movable through movements corresponding to movements of the test specimen temperature information transmitter circuit and being connected to the test specimen temperature information transmitter circuit for supplying power to the test specimen temperature information transmitter circuit;
   an isolator arrangement isolating the stationary power transmitter circuit mechanically and electrically from the movable power receptor circuit; and
   a power transfer system for passing power from the stationary power transmitter circuit across the isolator arrangement to the movable power receptor circuit without a direct mechanical or electrical connection between the stationary power transmitter and the movable power receptor circuit.

5. The improvement of claim 4 wherein the power transfer system comprises an induction arrangement including a primary induction coil in the power transmitter circuit, and a secondary induction coil in the power receptor circuit and juxtaposed with the primary induction coil for receiving, by induction, power from the primary induction coil.

6. The improvement of claim 5 wherein the isolator arrangement includes an air gap between the primary induction coil and the secondary induction coil.

7. An improvement in a rheometer in which strain is effected in a test specimen in order to measure a test parameter in the test specimen, the improvement comprising:
   a test parameter information sensor for juxtaposition in close proximity with the test specimen to provide information pertaining to a test parameter of the test specimen;
   a test parameter information transmitter circuit for receiving test parameter information from the test parameter information sensor;

the test parameter information sensor and the test parameter information transmitter circuit being movable through movements corresponding to the strain effected in the test specimen;

a test parameter information receptor circuit juxtaposed with the test parameter information transmitter circuit and being placed at a stationary location relative to the test parameter information transmitter circuit;

an isolator arrangement isolating the stationary test parameter information receptor circuit mechanically and electrically from the movable test parameter information transmitter circuit; and a test parameter information transfer system for passing test parameter information from the movable test parameter information transmitter circuit across the isolator arrangement to the stationary test parameter information receptor circuit without a direct mechanical or electrical connection between the movable test parameter information transmitter circuit and the stationary test parameter information receptor circuit.

8. The improvement of claim 7 wherein the test parameter information transfer system comprises an induction arrangement including a primary induction coil in the test parameter information transmitter circuit, and a secondary induction coil in the test parameter information receptor circuit and juxtaposed with the primary induction coil for receiving, by induction, test parameter information from the primary induction coil.

9. The improvement of claim 8 wherein the isolator arrangement includes an air gap between the primary induction coil and the secondary induction coil.

10. The improvement of claim 7, including:

a source of power;

a power transmitter circuit placed in a stationary location relative to the test parameter information transmitter circuit and being connected to the source of power;

a power receptor circuit juxtaposed with the power transmitter circuit for receiving power from the power transmitter circuit, the power receptor circuit being movable through movements corresponding to movements of the test parameter information transmitter circuit and being connected to the test parameter information transmitter circuit for supplying power to the test parameter information transmitter circuit;

an isolator arrangement isolating the stationary power transmitter circuit mechanically and electrically from the movable power receptor circuit; and a power transfer system for passing power from the stationary power transmitter circuit across the isolator arrangement to the movable power receptor circuit without a direct mechanical or electrical connection between the stationary power transmitter and the movable power receptor circuit.

11. The improvement of claim 10 wherein the power transfer system comprises an induction arrangement including a primary induction coil in the power transmitter circuit, and a secondary induction coil in the power receptor circuit and juxtaposed with the primary induction coil for receiving, by induction, power from the primary induction coil.

12. The improvement of claim 11 wherein the isolator arrangement includes an air gap between the primary induction coil and the secondary induction coil.

13. The improvement of claim 7 wherein the test parameter is temperature.

14. The improvement of claim 10 wherein the test parameter is temperature.

* * * * *